United States Patent
Kokones et al.

(10) Patent No.: US 8,676,342 B2
(45) Date of Patent: Mar. 18, 2014

(54) LEAD EXTENSION WITH INPUT CAPABILITIES

(75) Inventors: Scott Kokones, Boston, MA (US); Keith Carlton, Boston, MA (US)

(73) Assignee: Intelect Medical, Inc., Cleveland, OH (US)

(*) Notice: Subject to any disclaimer, the term of this patent is extended or adjusted under 35 U.S.C. 154(b) by 0 days.

(21) Appl. No.: 13/213,688

(22) Filed: Aug. 19, 2011

(65) Prior Publication Data

US 2011/0307031 A1  Dec. 15, 2011

Related U.S. Application Data

(63) Continuation of application No. 11/832,148, filed on Aug. 1, 2007, now Pat. No. 8,027,737.

(51) Int. Cl.
*A61N 1/05* (2006.01)

(52) U.S. Cl.
USPC .............................. 607/116; 607/45; 607/115

(58) Field of Classification Search
USPC .............................. 607/45, 115, 116; 600/544
See application file for complete search history.

(56) References Cited

U.S. PATENT DOCUMENTS

| | | | |
|---|---|---|---|
| 5,222,506 A | 6/1993 | Patrick et al. | |
| 5,314,353 A | 5/1994 | Schroeder | |
| 5,361,189 A | 11/1994 | Miyashita | |
| 5,406,957 A * | 4/1995 | Tansey | 600/545 |
| 5,439,391 A | 8/1995 | McEtchin et al. | |
| D372,785 S | 8/1996 | Sabri et al. | |
| 5,611,350 A * | 3/1997 | John | 600/378 |
| 5,782,892 A | 7/1998 | Castle et al. | |
| 5,931,861 A | 8/1999 | Werner et al. | |
| 6,038,479 A | 3/2000 | Werner et al. | |
| 6,038,481 A | 3/2000 | Werner et al. | |
| 6,192,278 B1 | 2/2001 | Werner et al. | |
| 6,343,233 B1 | 1/2002 | Werner et al. | |
| 6,532,379 B2 | 3/2003 | Stratbucker | |
| 6,602,202 B2 * | 8/2003 | John et al. | 600/559 |
| 6,605,094 B1 | 8/2003 | Mann et al. | |
| 6,671,544 B2 | 12/2003 | Baudino | |
| 6,705,887 B1 | 3/2004 | Fussell | |
| 6,743,055 B1 | 6/2004 | Flynn et al. | |
| 6,980,863 B2 | 12/2005 | van Venrooij et al. | |
| D523,557 S | 6/2006 | Jones et al. | |
| D525,708 S | 7/2006 | Jones et al. | |
| 7,128,600 B2 | 10/2006 | Osypka | |
| 7,130,699 B2 | 10/2006 | Huff et al. | |

(Continued)

OTHER PUBLICATIONS

Neurostimulation, http://www.painandwellness.com/spinal_injections_neurostimulation.html, accessed Mar. 28, 2011.

(Continued)

*Primary Examiner* — Allen Porter, Jr.
(74) *Attorney, Agent, or Firm* — Kenyon & Kenyon LLP

(57) ABSTRACT

A lead extension useful in deep brain stimulation treatment includes a body portion having a distal end and a proximal end, wherein the proximal end receives a stimulation signal from a generator. A lead interface is disposed at the distal end to send the stimulation signal to a brain stimulation lead. The lead extension also includes a sensor interface disposed at the distal end to receive an input signal from a sensor that is detached from the stimulation lead and send the input signal to the generator.

29 Claims, 5 Drawing Sheets

(56) References Cited

U.S. PATENT DOCUMENTS

| | | | |
|---|---|---|---|
| 2002/0077670 A1* | 6/2002 | Archer et al. | 607/45 |
| 2002/0091335 A1* | 7/2002 | John et al. | 600/544 |
| 2002/0177882 A1* | 11/2002 | DiLorenzo | 607/45 |
| 2003/0040784 A1 | 2/2003 | Pasternak et al. | |
| 2003/0077943 A1 | 4/2003 | Osypka | |
| 2003/0093130 A1 | 5/2003 | Stypulkowski | |
| 2003/0120327 A1 | 6/2003 | Tobritzhofer et al. | |
| 2003/0149456 A1 | 8/2003 | Rottenberg et al. | |
| 2004/0064172 A1 | 4/2004 | McVenes et al. | |
| 2004/0087207 A1 | 5/2004 | Lerch | |
| 2004/0186542 A1 | 9/2004 | van Venrooij et al. | |
| 2004/0230267 A1 | 11/2004 | Wenger | |
| 2004/0230268 A1 | 11/2004 | Huff et al. | |
| 2004/0230269 A1 | 11/2004 | Huff et al. | |
| 2004/0260355 A1 | 12/2004 | Holleman et al. | |
| 2004/0260373 A1 | 12/2004 | Ries et al. | |
| 2005/0070971 A1 | 3/2005 | Fowler et al. | |
| 2005/0203366 A1* | 9/2005 | Donoghue et al. | 600/378 |
| 2005/0205710 A1 | 9/2005 | Glasson | |
| 2005/0228249 A1 | 10/2005 | Boling | |
| 2005/0240242 A1 | 10/2005 | DiLorenzo | |
| 2005/0272280 A1 | 12/2005 | Osypka | |
| 2006/0190056 A1 | 8/2006 | Fowler et al. | |
| 2006/0229686 A1* | 10/2006 | Giftakis et al. | 607/45 |
| 2007/0167991 A1 | 7/2007 | DiLorenzo | |
| 2011/0071604 A1 | 3/2011 | Wahlstrand et al. | |

OTHER PUBLICATIONS

Medtronic DBS Extension Kit for Deep Brain Stimulation 7482A, Implant Manual, http://professional.medtronic.com/pt/neuro/dbs-md/prod/dbs-extension-model-7482/index.htm, accessed Mar. 28, 2011.

Medtronic Activa PC, Deep Brain Neurostimulator, Leads and Extensions, http://professional.medtronic.com/products/activa-pc-deep-brain-neurostimulator/leads-and-extensions/index.htm#tab2, accessed Mar. 28, 2011.

National Institute of Neurological Disorders and Stroke, National Institutes of Health, Deep Brain Stimulation for Parkinson's Disease Information Page, http://www.ninds.nih.gov/disorders/deep_brain_stimulation/deep_brain_stimulation.htm, accessed Mar. 28, 2011.

Medtronic Activa SC, Deep Brain Neurostimulator, Implant Procedure and Techniques, http://professional.medtronic.com/products/activa-sc-deep-brain-neurostimulator/implant-procedures-and-techniques/index.htm, accessed Mar. 28, 2011.

International Preliminary Report on Patentability, PCT/US2008/071731, Feb. 2, 2010.

PCT Notification of Transmittal of the International Search Report and the Written Opinioin of the International Searching Authority, or the Declaration dated Oct. 31, 2008.

Medtronic, Inc., "Dual Program Neurostimulator for Deep Brain Stimulation", Medtronic, Kinetra 7428 Technical Manual, pp. 1-63, http://manuals.medtronic.com/en/neuromodulation/implantable-neurostimulators/deep-brain-stimulators/index.htm, last accessed Aug. 19, 2011.

Medtronic, Inc, "Your Activa Therapy With a Kinetra or Soletra Neurostimulator", Medtronic Patient Manual, 2003, pp. 1-145, http://www.medtronic.com/downloadablefiles/220716003.pdf, accessed Aug. 19, 2011.

* cited by examiner

LEAD EXTENSION WITH INPUT CAPABILITIES

CROSS REFERENCE TO RELATED APPLICATION

This application is a continuation of U.S. Ser. No. 11/832,148, filed Aug. 1, 2007, which is hereby incorporated by reference in its entirety.

BACKGROUND

1. Technical Field

This disclosure generally relates to deep brain stimulation (DBS) systems. More particularly, the disclosure relates to lead extensions used in DBS systems.

2. Discussion

Deep brain stimulation (DBS) systems have begun to demonstrate clinical usefulness for a wide variety of conditions such as traumatic brain injury (TBI), stroke, Parkinson's disease, Essential Tremor, Dystonia and Parkinsonian tremor. Certain developments in DBS systems have centered around implantable neuro-stimulators, which are generators capable of delivering electrical pulses, physician programming devices, which enable the medical practitioner to tailor the electrical pulses for the desired application, and lead assemblies, which facilitate delivery of the electrical pulses from the generator to the targeted area of the brain. While conventional DBS systems have advanced rehabilitation and treatment in a number of areas, certain challenges remain.

One concern relates to assessing the results of DBS treatment. In particular, the typical DBS system might use a generator and lead assembly to deliver the electrical pulses to the brain, and a separate electroencephalogram (EEG) detector and electrodes to monitor the resulting brain activity. The ability to determine the relationship between the outgoing pulses and the resulting EEG activity may be limited due to the fact that the DBS system and EEG system reside on different platforms. Other solutions employ an EEG electrode at the tip of the stimulation lead in order to detect activity at the treatment site. This approach, however, does not provide the ability to obtain signals from other, less invasive, locations such as scalp locations or subcutaneous locations.

BRIEF DESCRIPTION OF THE DRAWINGS

The various advantages of the embodiments of the present invention will become apparent to one skilled in the art by reading the following specification and appended claims, and by referencing the following drawings, in which:

DETAILED DESCRIPTION

Embodiments of the present invention provide for a stimulation system having a generator, a brain stimulation lead, a sensor that is detached from the lead and a lead extension. The lead extension can be coupled to the generator, the lead and the sensor, wherein the generator produces a stimulation signal. The extension may include a body portion having a distal end and a proximal end, wherein the proximal end receives the stimulation signal from the generator. The extension can also include a lead interface disposed at the distal end to send the stimulation signal to the lead, and a sensor interface disposed at the distal end to receive an input signal from the sensor. By obtaining an input signal from a sensor that is detached from the lead, the system can exhibit much more flexibility with regard to monitoring and assessing patient DBS treatments. For example, sites other than the stimulation signal application site can be monitored and evaluated against the treatment being applied. In fact, much more robust closed-loop functionality may also be achievable, particularly if multiple sensors are used.

In other embodiments of the invention, a method of implementing deep brain stimulation system provides for receiving a stimulation signal from a generator and sending the stimulation signal to a brain stimulation lead via a lead extension. An input signal is received from a sensor that is detached from the stimulation lead and the input signal is sent to the generator via the lead extension. The input signal can include signals such as electroencephalogram (EEG) signals, acceleration signals, temperature signals, etc.

In other embodiments of the invention, a lead extension has a body portion, a lead interface and an electroencephalogram (EEG) interface. The body portion has a distal end, a proximal end, a signal line extending the proximal end and the distal end, and a multiplexer disposed at the distal end and coupled to the signal line. The proximal end receives a stimulation signal from a neuro-stimulation generator. The lead interface is disposed at the distal end of the body portion to send the stimulation signal to a brain stimulation lead. The EEG interface has a plurality of EEG connectors disposed at the distal end to receive a plurality of EEG signals from a plurality of EEG sensors that are detached from the stimulation lead. The EEG interface sends the EEG signals to the neuro-stimulation generator. The multiplexer can be further coupled to the plurality of EEG connectors and the lead interface, wherein the multiplexer may selectively couple each of the EEG connectors and the lead interface to the signal line.

Figure 1:
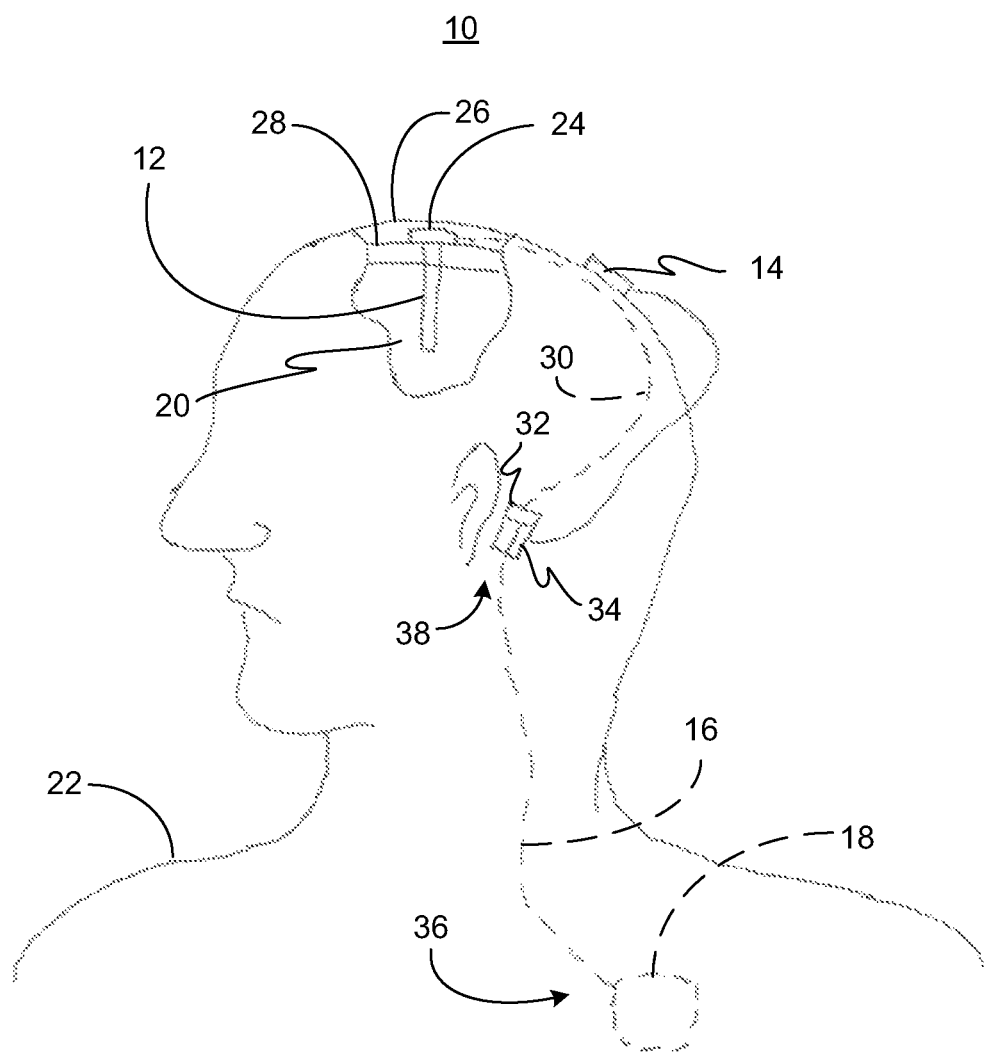
FIG. 1 is an environmental view of an example of a stimulation system according to an embodiment of the invention.

Turning now to FIG. 1, a deep brain stimulation (DBS) system 10 is shown, wherein the illustrated DBS system 10 includes a brain stimulation lead 12, a sensor 14 that is detached from the lead 12 and a lead extension 16 coupled to a generator 18 of a stimulation signal. The illustrated system 10 may be used to treat and/or rehabilitate patients with traumatic brain injury, Parkinson's disease or Parkinson's tremor, patients having suffered a stroke, as well as a wide variety of other brain related conditions. The stimulation lead 12 may have a distal end positioned at a treatment site in the brain 20 of a patient 22. A cap portion 24 of the lead 12 can be implanted between the scalp 26 and skull 28 of the patient 22, wherein the cap portion 24 may be electrically connected to the extension 16 by way of a wire 30. The illustrated wire 30, which may be a collection of wires, connects to the lead extension 16 through a lead interface 32, which may be positioned behind the ear of the patient 22. The lead 12 usually connects to the extension 16. The distal end of the lead 12 may be provided with a plurality of ring electrodes capable of delivering electrical pulses to the brain 20 of the patient 22 based on a stimulation signal from the generator 18. The electrodes may also be used to obtain input signals from the treatment area. The use of such lead-mounted electrodes, however, may involve the invasive procedure of implanting the brain stimulation lead 12 into the patient brain 20, and signals may generally only be obtained from the treatment site.

To increase the flexibility in obtaining information concerning the treatment and reduce the invasiveness of signal measurement, the DBS system 10 may use a sensor 14, which connects to the lead extension 16 via a sensor interface 34 and is a skin electrode that may be readily applied to the scalp 26 of the patient 22. The sensor 14 may alternatively be a subcutaneous lead that is placed under the scalp 26 but outside the skull 28 of the patient 22. The sensor 14 may be an electroencephalogram (EEG) electrode, an accelerometer, or any other type of sensor useful in evaluating DBS or other procedures. In fact, the sensor 14 can aid in evaluating status conditions of the patient 22, such as awareness (e.g., head movement), normal brain function as determined by EEG, or seizures. The information obtained from the sensor 14 may also be used to determine subsequent positioning of the lead 12.

With regard to use of the sensor 14 as an EEG sensor, electroencephalography is the neurophysiologic measurement of the electrical activity of the brain by recording from electrodes placed on the scalp, or, in certain cases, subdurally or in the cerebral cortex. The resulting traces are known as an EEG and represent an electrical signal (postsynaptic potentials) from a large number of neurons. The EEG is a brain function test, but in clinical use it is a gross correlate of brain activity. Electrical currents are not measured but rather voltage differences between different parts of the brain. EEGs are desirable for use in experimentation because the process is non-invasive to the research subject. The subject may not need to make a decision or behavioral action in order to log data, and the EEG can detect covert responses to stimuli, such as reading. The EEG is also capable of detecting changes in electrical activity in the brain on a millisecond-level. It is one of the few techniques available that has such high temporal resolution.

Accelerometer data may also be useful to track head movement before, during, and after various stimuli. Multiple accelerometers may be useful to determine rotational or relative movement. Similarly, multiple EEG electrodes may be used to provide greater resolution regarding the voltage differences between different parts of the brain. Thus, although a single sensor 14 is shown in the illustrated embodiment, multiple sensors may be used. In addition, the sensor 14 may communicate wirelessly with the distal end 38 of the extension 16, or may be mounted on the extension 16 itself.

In operation, the body portion of the illustrated extension 16 has a proximal end 36 that receives the stimulation signal from the generator 18 (e.g., via an electrical plug), and a distal end 38 that uses the lead interface 32 to send the stimulation signal to the lead 12. The extension 16 may also use the sensor interface 34 to receive the input signal from the sensor 14. All of the illustrated components are implantable. For example, the generator 18 may be implanted by placing the generator 18 in a subcutaneous pocket created by making a blunt dissection in the subclavicular region, wherein the generator 18 can include one or more suture holes (not shown) for securing the generator 18 to the muscle facia. In addition, the lead 12 may be tunneled to the distal end of the extension 16, and the extension 16 may be tunneled to the generator 18 using well known implantation procedures. The sensor 14 may be mounted outside the scalp 26 (e.g., similar to a traditional EEG electrode), wherein the sensor 14 can be registered with the system 10 and report data wirelessly.

Figure 2:
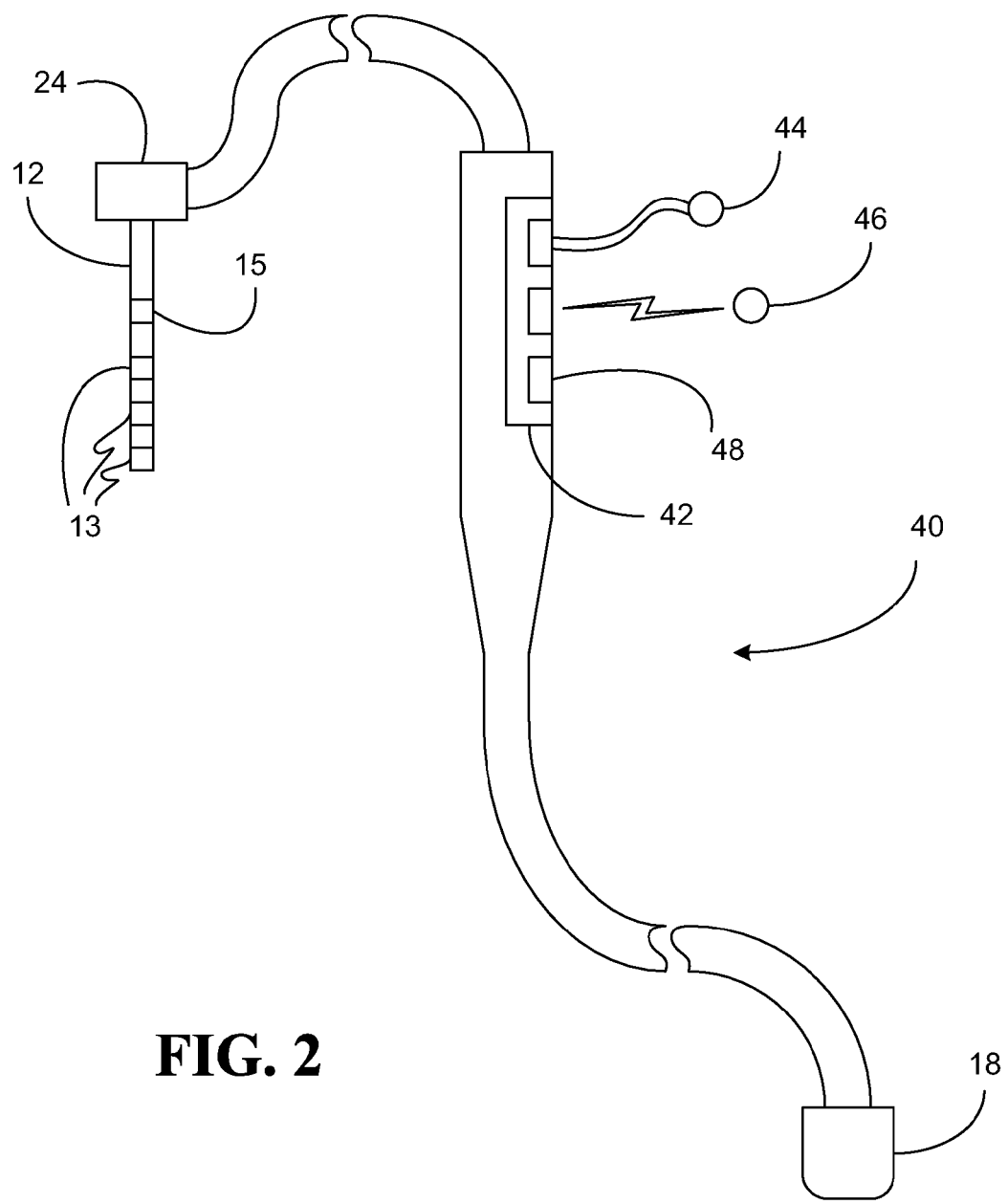
FIG. 2 is a diagram of an example of a lead extension having localized and remote sensing functionality according to an embodiment of the invention.

FIG. 2 shows an alternative embodiment of a lead extension 40 in which the sensor interface 42 provides connectivity to a remote wired sensor 44, a remote wireless sensor 46 and a local integrated sensor 48. The remote wired sensor 44 can plug into an electrical connector having a female/socket contact configuration, which mates with a male/plug contact configuration of the free end of the wire connected to the sensor 44. The number of contacts may vary depending on circumstances such as the grounding scheme, signaling scheme (e.g., single-ended/unipolar signaling, differential/bipolar signaling), and so on. The remote wireless sensor 46 may communicate with the sensor interface 42 using any appropriate wireless signaling protocol. An example of a suitable wireless sensor is the Tmote Mini sensor commercially available from Moteiv Corporation of San Francisco, Calif. The local integrated sensor 48 can be molded into the silicone or polyurethane distal end of the extension 40 or coupled to the sensor interface 42 by surface mount technology (SMT), which is a method for constructing electronic circuits in which the components are mounted directly onto the surface of printed circuit boards (PCBs) and other substrates. The structure of the integrated sensor 48 may be similar to that of surgical leads that are used for spinal cord stimulation or cortical leads used for EEG monitoring of epilepsy patients. For example, the local integrated sensor 48 can have an exposed platinum or other metallic surface for data collection.

The lead 12 may include one or more electrodes 13 as well as a lead sensor 15, which can be used to extract EEG data from the stimulation signal delivery site. The placement of the illustrated lead sensor 15 is dictated by the placement of the lead 12, whereas the sensors 44, 46, 48 may be disposed at any desired location on or near the patient. Meanwhile, all input signals and brain stimulation signals may be transferred between the patient and the generator 18 using the lead extension 40. Although the sensors 44, 46, 48 may also be located on other portions of the system such as the burr hole cap 24 or lead 12, the illustrated example demonstrates the enhanced flexibility of a lead extension that communicates with sensors that are detached from the brain stimulation lead. Other placements for one or more of the sensors 44, 46, 48 include, but are not limited to, the implantable pulse generator 18, an external pulse generator (not shown), and a patient programmer (not shown).

For example, a sensor mounted to a patient programmer could interact with sensors external to the patient programmer to give a more complete view of the patient recovery. In particular, a motion sensor in the patient programmer could interact with a sensor held by the patient during rehabilitation tasks. This interaction could indicate the distance traveled by the patient's extremity during the course of a specific rehabilitation task. Another example is that a motion sensor in the patient programmer could interact with a sensor implanted in the patient as part of the implantable therapeutic system. One possibility is that the interaction of these sensors could indicate overall movement of the patient in both body and head movement, which could be informative as to the overall rehabilitation status of the patient.

Figure 3:
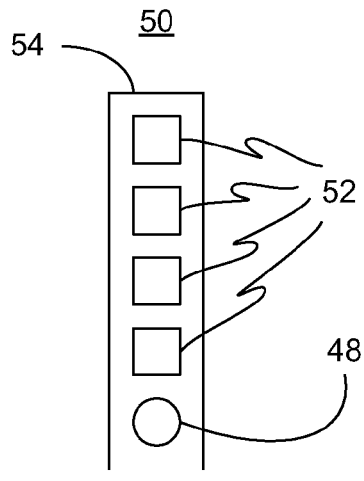
FIG. 3 is a bottom view of an example of a lead extension having localized sensing functionality according to an embodiment of the invention.

Turning now to FIG. 3, another example of a lead extension 50 is shown. In this example, the bottom surface of an extension 50 has a plurality of set screw openings 52, wherein set screws may be inserted into the openings 52 in order to mate the contacts of the extension 50 with the contacts of a brain stimulation lead (not shown) that is inserted into the distal end 54 of the extension 50. There may also be "toolless" connections to the lead such as Ball Seals, which connect electrically but do not involve mechanical fixation with a wrench. The illustrated extension 50 also includes an integrated sensor 48 that may be pressed against the scalp (e.g., behind the ear) of the patient in order to obtain signals such as EEG signals or acceleration signals.

Figure 4:
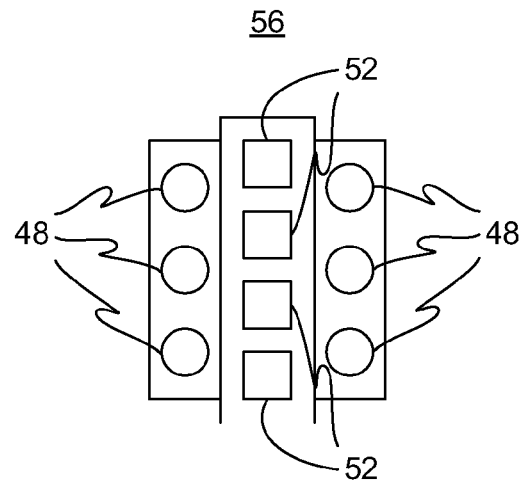
FIG. 4 is a bottom view of an example of a lead extension having an array of localized sensing inputs according to an embodiment of the invention.

FIG. 4 shows another example in which an array of surface mounted sensors 48 are coupled to the bottom surface of an extension 56 in a "wing" formation. Each sensor 48 may collect the same or different types of data from the patient, depending on the circumstances. For example, the sensors on the left of the extension might obtain EEG data, whereas the sensors on the right of the extension could obtain thermal measurements.

Figure 5:
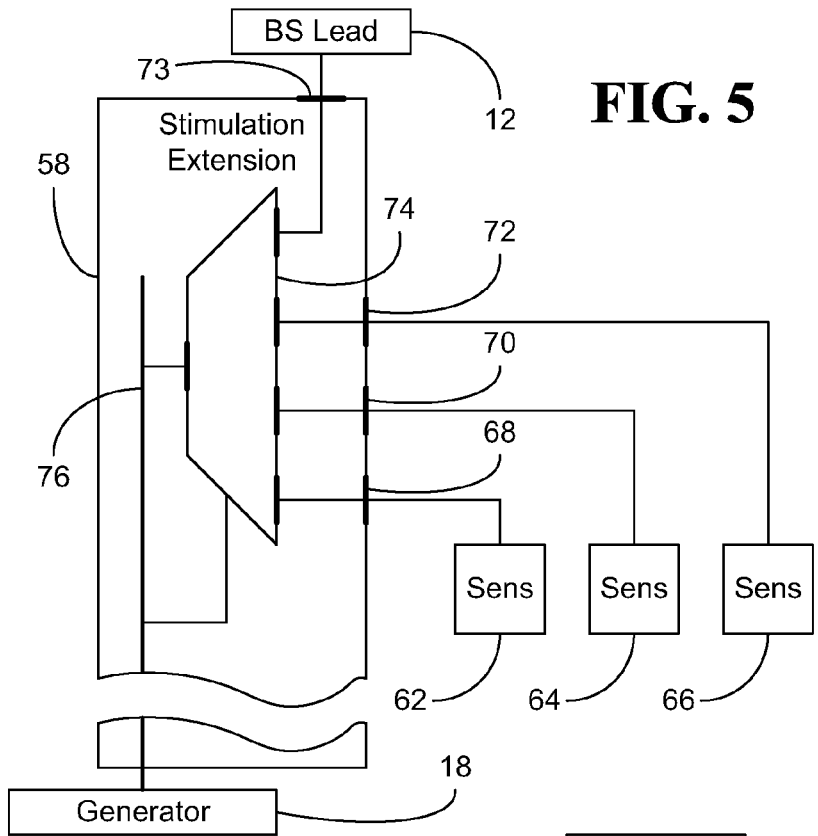
FIG. 5 is a schematic diagram of an example of a lead extension having a wired architecture according to an embodiment of the invention.

Turning now to FIG. 5, a schematic of a lead extension 58 having connectivity to a brain stimulation lead 12 and a plurality of remote wired sensors 62, 64, 66 is shown. In the illustrated example, a body portion of the lead extension 58 includes a plurality of electrical connectors 68, 70, 72, which provide a connection to the remote wired sensors 62, 64, 66. The connectors 68, 70, 72 may be standard EEG electrode connectors, or any other type of connector depending upon the type of sensor. The illustrated connectors 68, 70, 72, which are disposed at the distal end of the lead extension 58, may be coupled to a multiplexer 74. The multiplexer 74 may also be coupled to the brain stimulation lead 12 via a lead connector 73 and coupled to a signal line 76, which may include multiple conductors. The illustrated signal line 76 can extend, for example, through a plastic (e.g., polyurethane, silicone, ETFE, PTFE) sheath or conduit, between the proximal end and the distal end of the lead extension 58. The use of the illustrated multiplexer 74 can reduce the number of conductors required in the signal line 76 and ultimately reduce the size of the body portion (e.g., sheath diameter) of the extension 58. The multiplexer 74 may be a digital or analog multiplexer, and the operating characteristics of the multiplexer 74 can be selected based on the power, voltage and current properties of the anticipated stimulation signals and/or input signals to be used in the DBS system.

The illustrated multiplexer 74 is able to selectively couple the signal line 76 to the brain stimulation lead 12 and to each of the connectors 68, 70, 72. The multiplexer 74 may use a selection signal, which can be obtained from the signal line 76, to determine which connection scheme to use. Thus, in operation, the generator 18 may place a connector selection signal onto the signal line 76, instructing the multiplexer 74 to connect the signal line 76 to the brain stimulation lead 12. The generator 18 may then send the desired stimulation signal down the signal line 76 through the multiplexer 74 and to the brain stimulation lead 12. The generator 18 can then send an input selection signal down the signal line 76, to instruct the multiplexer 74 to couple one or more of the electrical connectors 68, 70, 72, to the signal line 76 so that the generator may obtain the input signals from the sensors 62, 64, 66.

The latching of the electrical connectors 68, 70, 72 to the signal line 76 may be a serial latching scheme in which the sensor inputs are collected one after another, or a parallel latching scheme in which the sensor inputs are combined. In any event, the generator 18 may store the input signals for later retrieval by a clinician programmer or patient programmer, or use the input signals in a real-time closed loop fashion to select, formulate, and generate subsequent stimulation signals.

In this regard, the generator 18 may have a wide range of noninvasively programmable parameters and stimulation modes, and can exchange parameter information, via telemetry, with a clinician programmer and/or a patient programmer. The stimulation pulses delivered to each brain stimulation lead can be determined by a parameter called a program, wherein a program can be a specific combination of amplitude, rate and pulse width parameters acting on a specific brain stimulation lead electrode set. For the stimulation signals, example current outputs may range from 0-20 mA, example pulse widths may range from 10-1000 μs per phase, example frequencies may range from 1-1200 Hz, and the waveform shape might be square, sine or triangle wave. Other parameter ranges and characteristics may also be used. The generator 18 may be designed to adjust and/or supplement these parameters based on the input signals from sensors such as the sensors 62, 64, 66.

In one embodiment, a clinician programmer (not shown) can be used to determine which programs are to be run on the generator 18 and may display instruction prompts for the user and show parameter data. The clinician programmer can also be used to provide stimulation parameters and patient programmer adjustment limits for multiple programs, collect measurements and diagnostic data from the generator 18 based on the input signals from the sensors 62, 64, 66, and may be used to switch the generator 18 on and off, and obtain the battery status of the generator 18, which may be powered by a hermetically sealed silver vanadium oxide cell, a lithium ion cell, or other state of the art battery chemistries. In particular, upon interrogation by a clinician programmer, the generator 18 might transmit via an RF link to the clinician programmer for display or printing: model and serial number identification, programmed parameters and values, generator battery status, number of patient activations (since last reset), total stimulation time (since last reset), elapsed time (since last reset) and verification of program changes. After a program entry, the clinician programmer can compare stimulation signal parameters, via telemetry, with the entries made during programming.

A patient programmer (not shown) can be used by the patient to switch the generator 18 on and off, obtain the on and off status of the generator 18, adjust the stimulation parameters within physician prescribed limits for multiple programs, and obtain the battery status of the generator 18.

Figure 6:
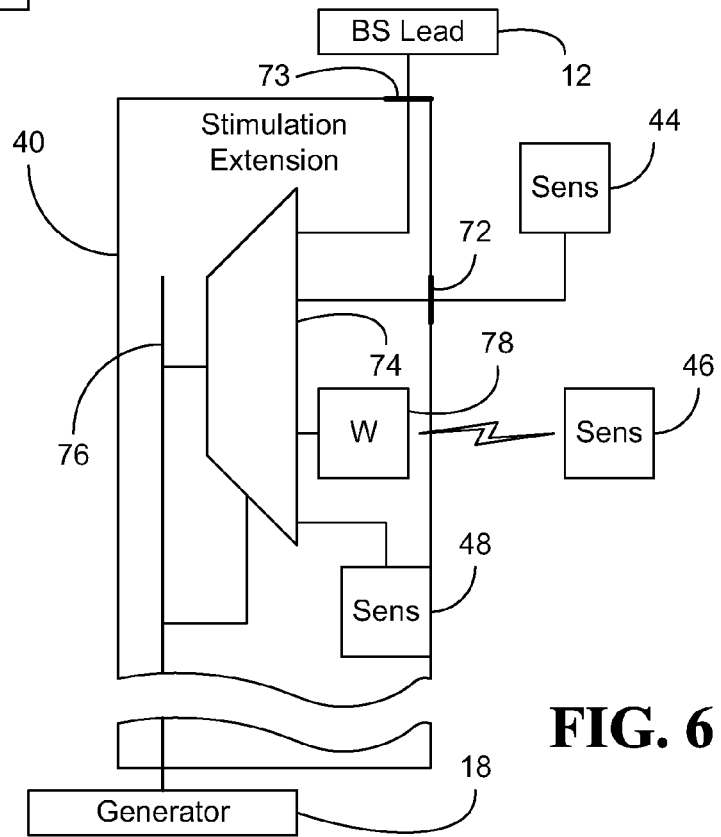
FIG. 6 is a schematic diagram of an example of a lead extension having a wireless architecture and a wired architecture according to an embodiment of the invention.

FIG. 6 shows a lead extension 40 having localized surface mount, remote wired, and remote wireless functionality. In the illustrated example, which is similar to an example discussed above (FIG. 2), the lead extension 40 is able to pass stimulation signals from the generator 18 to the brain stimulation lead 12, as well as obtain input signals from a remote wired sensor 44, a wireless sensor 46 and a surface mounted sensor 48. The input signals from the wired sensor 44 may be obtained via an electrical connector 72, whereas the input signals from the wireless sensor 46 may be collected via a wireless interface 78. The wireless interface may include communication modules such as radio frequency (RF) telemetry modules, WiFi (Wireless Fidelity; e.g., IEEE 802.11) modules, Bluetooth (e.g., IEEE 802.15.1) modules and WPAN (Wireless Personal Area Network; e.g., IEEE 802.15.4) modules, etc. The surface mount sensor 48 may be connected directly to the multiplexer 74. Thus, the multiplexer 74 may selectively couple the brain stimulation lead 12, and each of the sensors 44, 46, 48 to the signal line 76 as needed.

Figure 7:
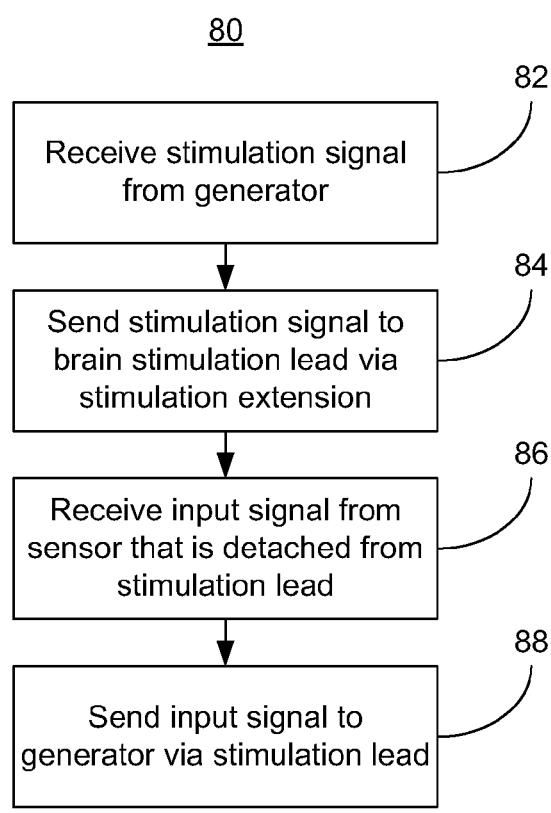
FIG. 7 is a flowchart of an example of a method of conducting deep brain stimulation according to an embodiment of the invention.

Turning now to FIG. 7, a method 80 of conducting deep brain stimulation is shown. The method 80 may be implemented in a lead extension using analog, digital, wireless, mechanical, chemical and/or other technologies as appropriate. In the illustrated example, a stimulation signal is received from a generator at processing block 82. Block 84 provides for sending the stimulation signal to a brain stimulation lead via a lead extension. An input signal is received from a sensor that is detached from the stimulation lead at block 86. Block 88 provides for sending the input signal to the generator via the lead extension. As already noted, the input signal may be a wide variety of input signals such as EEG signals, acceleration signals, temperature signals, etc. In the case of acceleration signals, multiple accelerometers may be used in order to determine directional movement of the patient's head.

Figure 8:
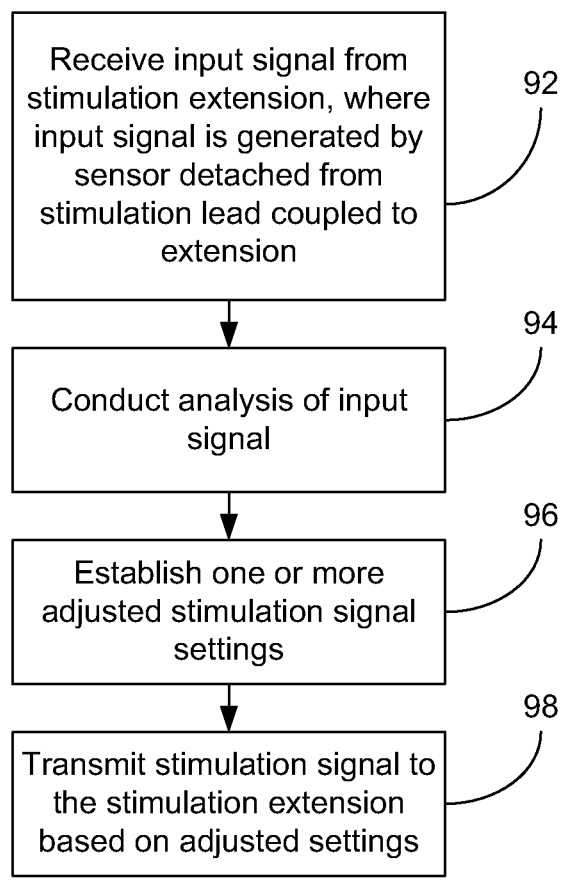
FIG. 8 is a flowchart of an example of a method of processing an input signal according to an embodiment of the invention.

FIG. 8 shows a method 90 of processing an input signal received from a sensor via a lead extension. The method 90 may be implemented in a neuro-stimulation generator as a set of processor-executable instructions stored in ROM, RAM, electrically erasable programmable ROM (EEPROM), flash memory, etc., as fixed functionality hardware such as an embedded microcontroller, application specific integrated circuit (ASIC), etc. using complementary metal oxide semiconductor (CMOS) technology or transistor-transistor-logic (TTL), or any combination thereof. Illustrated processing block 92 provides for receiving an input signal from a lead extension, wherein the input signal is generated by a sensor that is detached from a stimulation lead coupled to the extension. An analysis of the input signal can be conducted at block 94 and one or more adjusted settings of a stimulation signal can be established based on the analysis at block 96. Block 98 provides for transmitting the stimulation signal to the stimulation extension based on the adjusted settings. The processes of the method 90 may also be repeated until a threshold such as a stimulation performance and/or patient response threshold is met. Thus, the illustrated method 90 provides for a closed loop operation of a system such as a DBS system, so that stimulation signals can be adjusted in real-time to achieve a greater level of performance than achievable under conventional approaches.

The terms "connected", "coupled" and "attached" are used herein to refer to any type of relationship, direct or indirect, between the components in question, and may apply to electrical, mechanical, RF, optical or other couplings. In addition, the term "first", "second", and so on are used herein only to facilitate discussion, and do not necessarily infer any type of temporal or chronological relationship.

Those skilled in the art will appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specifications, and following claims.

What is claimed is:

1. A lead extension arrangement configured to connect a brain stimulation lead to a neuro-stimulation generator comprising:
   an interface arrangement; and
   a lead extension;
   wherein:
      a proximal end of the lead extension is connected to, and is configured to receive a stimulation signal from, a neuro-stimulation generator;
      the interface arrangement includes a component in which are integrated a lead interface, an electroencephalogram (EEG) interface separate from the lead interface, and a lead extension interface separate from the lead and EEG interfaces;
      the EEG interface is connected to, and configured to receive a plurality of EEG signals from, a plurality of EEG sensors at least one of which is detached from the brain stimulation lead and is adapted to be disposed at least one of on a scalp, and between the scalp and a skull, of a patient;
      the lead extension interface is connected to a distal end of the lead extension and is configured to (a) provide the plurality of EEG signals to the neuro-stimulation generator via the lead extension and (b) obtain the stimulation signal from the lead extension; and
      the lead interface is connected to, and configured to send the stimulation signal to, the brain stimulation lead.

2. The lead extension arrangement of claim 1, further including an accelerometer interface integrated in the component of the interface arrangement and configured to receive an acceleration signal from an accelerometer that is detached from the brain stimulation lead and configured to send the acceleration signal to the neuro-stimulation generator.

3. The lead extension arrangement of claim 1, wherein the lead interface is configured to receive a lead signal from a lead sensor attached to the brain stimulation lead and the interface arrangement is configured to send the lead signal to the neuro-stimulation generator.

4. The lead extension arrangement of claim 1, wherein the EEG interface includes an electrical interface.

5. The lead extension arrangement of claim 1, wherein at least one EEG sensor is molded to the distal end of the extension.

6. The lead extension arrangement of claim 1, wherein the EEG interface further includes a wireless interface.

7. The lead extension arrangement of claim 6, wherein the wireless interface includes a communication module selected from a group comprising a radio frequency module, a WiFi module, a Bluetooth module and a WPAN module.

8. The lead extension of claim 1, wherein at least one EEG sensor is disposed on the lead extension.

9. The lead extension of claim 1, wherein the brain stimulation lead includes a sensor that obtains data from a tissue site at which stimulation occurs using the stimulation signal, and the interface arrangement is configured to send the data over the lead extension to the neuro-stimulation generator.

10. The lead extension of claim 9, wherein the data is EEG data.

11. The lead extension of claim 9, wherein the sensor that obtains the data is implanted in a brain.

12. The lead extension arrangement of claim 1, wherein the brain stimulation lead includes a shaft on which at least one stimulation electrode is arranged, the at least one stimulation electrode being configured to produce an electric stimulation based on the stimulation signal.

13. The lead extension arrangement of claim 1, wherein the at least one EEG sensor is adapted to be disposed between the scalp and the skull of the patient.

14. A stimulation system comprising:
   a generator configured to generate a stimulation signal;
   a brain stimulation lead; and
   a lead extension arrangement configured to be coupled to the generator and the lead, the lead extension arrangement including an interface arrangement and a lead extension;
   wherein:

a proximal end of the lead extension is connected to, and is configured to receive the stimulation signal from, the generator;

the interface arrangement includes a component in which are integrated a lead interface, a sensor interface separate from the lead interface, and a lead extension interface separate from the lead and sensor interfaces;

the sensor interface is connected to, and configured to receive an input signal from, a sensor that is (a) detached from the brain stimulation lead and (b) adapted to be disposed at least one of on a scalp, and between the scalp and a skull, of a patient;

the lead extension interface is connected to a distal end of the lead extension and is configured to (a) provide the input signal from the sensor to the generator via the lead extension and (b) obtain the stimulation signal from the lead extension; and the lead interface is connected to, and configured to send the stimulation signal to, the brain stimulation lead.

15. A method of neuro-stimulation by a stimulation system, the system including a neuro-stimulator that is coupled, via a lead extension arrangement, to a brain stimulation lead that includes at least one electrode, wherein: (i) the lead extension arrangement includes a lead extension and an interface arrangement, (ii) a proximal end of the lead extension is connected to the neuro-stimulator, (iii) the interface arrangement includes a component in which are integrated a lead interface, an electroencephalogram (EEG) interface separate from the lead interface, and a lead extension interface separate from the lead and EEG interfaces, (iv) the lead interface is connected to the brain stimulation lead, (v) the EEG interface is connected to a plurality of EEG sensors at least one of which is detached from the brain stimulation lead and disposed at least one of on a scalp, and between the scalp and a skull, of a patient, and (vi) the lead extension interface is connected to a distal end of the lead extension, the method comprising:

(a) receiving, at the neuro-stimulator, a plurality of EEG signals of one or more of the plurality of EEG sensors via a transmission path by which the EEG signals are (1) provided to the interface arrangement via the EEG interface, (2) subsequently provided to the lead extension over the lead extension interface, and (3) subsequently provided to the neuro-stimulator from the lead extension;

(b) generating a stimulation signal with the neuro-stimulator in response to the plurality of EEG signals;

(c) providing the generated stimulation signal from the neuro-stimulator and onto the lead extension at the proximal end of the lead extension;

(d) sending the stimulation signal, from the lead extension and by the lead extension and lead interfaces, to the brain stimulation lead; and (e) stimulating a tissue site via the at least one electrode on the brain stimulation lead using the stimulation signal.

16. The method of claim 15, further comprising sending an input signal from an accelerometer to the generator via the lead extension, the accelerometer being coupled to the lead extension and wherein the input signal includes an acceleration signal.

17. A method of neuro-stimulation by a stimulation system, the system including a neuro-stimulator coupled, via a lead extension arrangement, to a brain stimulation lead that includes at least one electrode, wherein: (i) the lead extension arrangement includes a lead extension and an interface arrangement, (ii) a proximal end of the lead extension is connected to the neuro-stimulator, (iii) the interface arrangement includes a component in which are integrated a lead interface, an electroencephalogram (EEG) interface separate from the lead interface, and a lead extension interface separate from the lead and EEG interfaces, (iv) the lead interface is connected to the brain stimulation lead, (v) the EEG interface is connected to a plurality of EEG sensors at least one of which is detached from the brain stimulation lead and disposed at least one of on a scalp, and between the scalp and a skull, of a patient, and (vi) the lead extension interface is connected to a distal end of the lead extension, the method comprising:

(a) generating a stimulation signal with the neuro-stimulator;

(b) receiving, at the neuro-stimulator, an input signal from at least one of the plurality of EEG sensors via a transmission path by which the input signal (1) is provided to the interface arrangement via the EEG interface, (2) subsequently provided to the lead extension over the lead extension interface, and (3) subsequently provided to the neuro-stimulator from the lead extension;

(c) conducting an analysis of the input signal with a processor within the neuro-stimulator;

(d) adjusting a setting of the stimulation signal based on the analysis of the input signal;

(e) providing the adjusted stimulation signal from the neuro-stimulator and onto the lead extension at the proximal end of the lead extension;

(f) sending the adjusted stimulation signal, from the lead extension and by the lead extension and lead interfaces, to the brain stimulation lead; and (g) stimulating a tissue site via the at least one electrode on the brain stimulation lead using the stimulation signal.

18. The method of claim 17, further including repeating steps (b)-(g).

19. A lead extension arrangement configured to connect a brain stimulation lead to a neuro-stimulation generator comprising:

a lead extension connected at a first end to the neuro-stimulation generator and extending from the first end to a second end at which an interface component is disposed, wherein:

the interface component includes (a) a first interface arrangement interfacing between a sensor and the second end of the lead extension, and (b) a second interface arrangement interfacing between the brain stimulation lead and the second end of the lead extension;

the first interface arrangement is configured to provide a signal from the sensor to the lead extension;

the lead extension is configured to provide the signal received via the first interface arrangement to the neuro-stimulation generator; and the lead extension is configured to obtain a stimulation signal from the neuro-stimulation generator and provide the obtained stimulation signal to the brain stimulation lead via the second interface arrangement for conducting an electrical stimulation based on the stimulation signal using electrodes of the brain stimulation lead.

20. The lead extension arrangement of claim 19, wherein the interface component includes a multiplexer that is configured to switch between a communicative coupling of the first interface arrangement to the lead extension and a communicative coupling of the second interface arrangement to the lead extension.

21. The lead extension arrangement of claim 20, wherein the sensor is one of a plurality of sensors, the first interface arrangement interfaces between the plurality of sensors and the second end of the lead extension, and the multiplexer further switches between communicative couplings of different ones of the sensors and the second end of the lead extension.

22. The lead extension arrangement of claim 19, wherein the sensor is one of a plurality of sensors adapted for being implanted in different anatomical regions apart from the electrodes, and the first interface arrangement interfaces between the plurality of sensors and the second end of the lead extension.

23. The lead extension arrangement of claim 22, wherein the plurality of sensors are not adapted for conducting the electrical stimulation.

24. The lead extension arrangement of claim 22, wherein the plurality of sensors are adapted for being implanted between a scalp and a skull of a patient.

25. The lead extension arrangement of claim 19, wherein the brain stimulation lead includes a shaft configured for being implanted in a skull of a patient and on which the electrodes are arranged, a cap portion configured for being implanted between the skull and a scalp of the patient when the shaft is implanted in the skull, and a wire extending from the cap portion to the second interface arrangement.

26. The lead extension arrangement of claim 19, wherein the brain stimulation lead includes a shaft configured for being implanted in a skull of a patient and on which the electrodes are arranged and a wire that electrically couples the electrodes to the second interface arrangement, and the wire and the lead extension are adapted for the interface component to be positioned behind an ear of the patient when the brain stimulation lead is implanted in the skull and the neurostimulation generator is implanted in a subclavicular region.

27. The lead extension arrangement of claim 26, wherein the sensor is integrated with the interface component.

28. The lead extension arrangement of claim 19, wherein the sensor is one of a plurality of sensors adapted for being positioned at different anatomical locations apart from the electrodes, and the first interface arrangement interfaces between the plurality of sensors and the second end of the lead extension.

29. The lead extension arrangement of claim 19, wherein the sensor is an electroencephalogram (EEG) sensor.

* * * * *